United States Patent [19]

Fleury, Jr.

[11] 4,096,855
[45] Jun. 27, 1978

[54] INCENTIVE SPIROMETER

[76] Inventor: George J. Fleury, Jr., 1005 Abbey Way, McLean, Va. 22101

[21] Appl. No.: 753,466

[22] Filed: Dec. 22, 1976

[51] Int. Cl.² .................................................. A61B 5/08
[52] U.S. Cl. .................... 128/2.08; 73/239; 92/98 D; 272/99
[58] Field of Search .................. 128/2.08, 2.07, 2 C; 73/239, 262; 92/98 D, 98 R; 272/99

[56] References Cited

U.S. PATENT DOCUMENTS

| | | | |
|---|---|---|---|
| 2,860,017 | 11/1958 | Honegger | 92/98 D |
| 3,319,420 | 5/1967 | Mercier | 92/98 D X |
| 3,395,699 | 8/1968 | Beasley | 128/2.08 |
| 3,635,214 | 1/1972 | Rand | 128/2.08 |
| 3,722,506 | 3/1973 | McMillan, Jr. | 128/2.08 |
| 3,754,546 | 8/1973 | Cooper | 128/2.08 |
| 3,848,583 | 11/1974 | Parr | 128/2.08 |
| 3,985,124 | 10/1976 | Coleman | 128/2.08 |

FOREIGN PATENT DOCUMENTS

| | | | |
|---|---|---|---|
| 1,569,193 | 5/1969 | France | 128/2.08 |
| 2,406,773 | 9/1974 | Germany | 128/2.08 |
| 503,395 | 12/1954 | Italy | 92/98 D |
| 489,502 | 2/1976 | U.S.S.R. | 128/2.08 |

*Primary Examiner*—Robert W. Michell
*Assistant Examiner*—Lee S. Cohen
*Attorney, Agent, or Firm*—Eric P. Schellin

[57] ABSTRACT

There is disclosed an incentive spirometer for measuring, as desired, the inspiratory breathing capacity and/or the expiratory breathing capacity including a freely floating piston positioned within a chamber. The piston is responsive to an inspired breath inhaled from one end of the chamber and also responsive to an exhaled breath introduced into the other end of the chamber. A novel rolling seal is provided which causes extremely minute friction losses during movement and which effectively seals the area between the external perimeter of the piston and the internal surface of the chamber.

9 Claims, 7 Drawing Figures

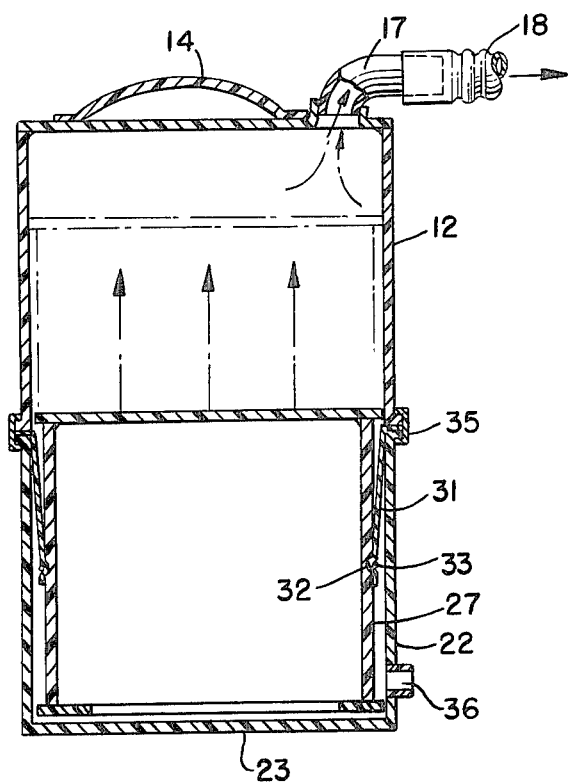
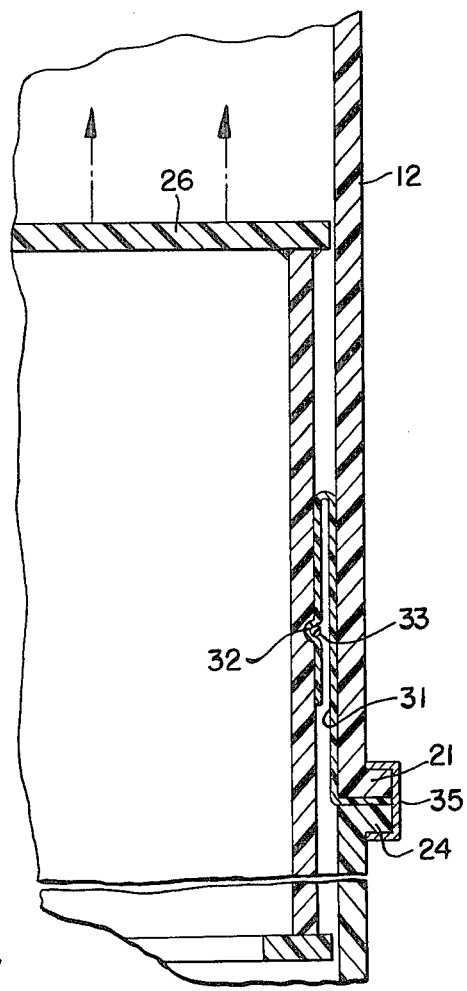
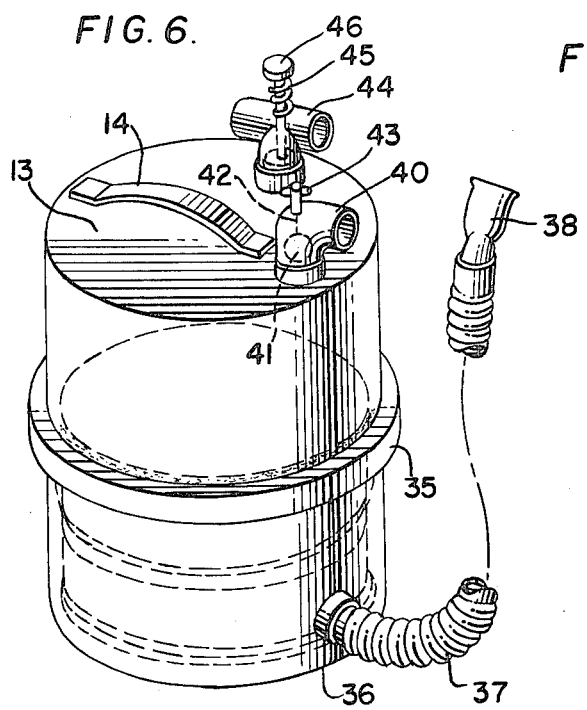
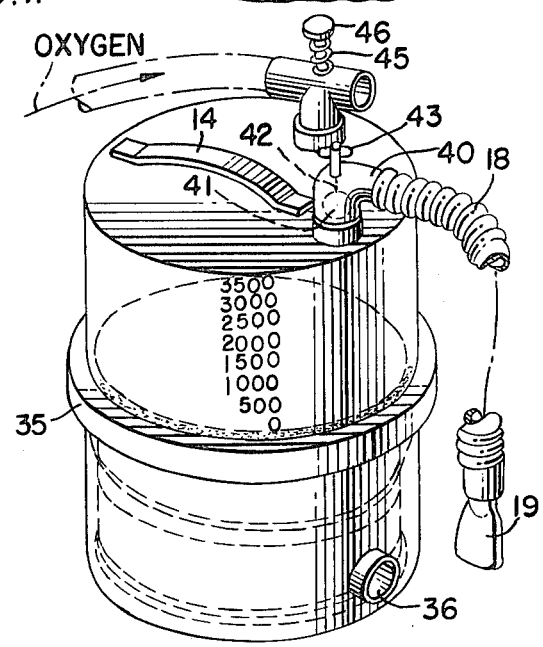

INCENTIVE SPIROMETER

BACKGROUND OF THE INVENTION

This invention relates to spirometers, especially portable spirometers having utility for early diagnosis of possible respiratory ailments and for monitoring the response of a patient to treatment. More importantly, perhaps, as the invention is designed to be an incentive inspirometer the invention is designed to encourage voluntary sustained maximal inspiration.

It is known that the absence of periodic deep breathing following abdominal or thoracic surgery may lead to gross atelectasis, hypoxia, and possible shunting caused by progressive alveolar collapse. It has been discovered that the incidence of pulmonary complications is decreased by voluntary rhythmic inspiration to total lung capacity which desirably inflates the lungs and prevents or reverses alveolar collapse.

The physiologic effects of sustained maximal inspiration have been studied in normal volunteers and postoperative patients. It has been noted that as intrathoracic pressure decreases to approximately minus 50 cm $H_2O$ and the lungs are filled to their capacity, all alveoli open, venous return is increased, stroke volume increases transiently, ventilation and perfusion equilibrate, and arterial oxygen increases. Alkalosis due to hypocapnia does not occur as long as maximal inspiration is repeated slowly (four to five times per minute, for instance). Therefore, to be effective, a respiratory maneuver must include high alveolar inflating pressure applied over an extended period of time.

There are at least two general types of spirometer presently in use; that is, the open-circuit spirometers and the closed-circuit spirometers. The open-circuit spirometer is characterized by a means to detect the desired pulmonary functions without containing the patient's expired air or in providing a known volume of air to be inspired. Such prior art instruments typically utilize a single or a plurality of Pitot-tube type detection devices. The devices, however, normally require relatively expensive electronic circuitry to obtain a readable function from the detected breathing qualities, and particularly in maintaining linearity of the instruments.

The closed-circuit spirometer of which the present invention is an example, normally includes a means to contain a supply of air for inspiration and/or the patient's exhaled breath and thereby measure the vital functions by some mechanical means associated with an expandable chamber. In the prior art closed-circuit spirometers, a unique problem arises in insuring a sufficiently protective seal between relative moving components or bellows, yet which does not introduce sufficient friction loss into the overall system to affect the accuracy of the measurements.

A number of prior art patentees have attempted to solve the sealing problem by employing what they term to be a U-shaped rolling seal. Attention with regard thereto is made to the teachings of Robert D. McMillan, Jr., U.S. Pat. No. 3,722,506, and Eric W. Staines, U.S. Pat. No. 3,848,583. However, the prior art patentees failed to solve many additional problems as are now solved by the present invention.

SUMMARY OF THE INVENTION

In accordance with the present invention, there is provided an improved spirometer having the capability of providing excellent accurate readings of a pulmonary function. As was stated, the spirometer is of the closed circuit type and utilizes a movable piston fitted within a closed cylinder provided with suitable ports. In one form of use the patient inspires a breath from a port means at the end of the cylinder and causes the piston to move a distance in proportion to the patient's ability to inspire. In another form of use of the invention the patient's expired breath is introduced into the other end portion of the cylinder which also causes the piston to move a distance in proportion to the patient's tidal volume.

A unique seal is provided between the outer perimeter of the movable piston and the interior of the cylinder in order to prevent any leakage therebetween. The seal is characterized by low friction or hysteresis during movement, and has substantially no memory, yet it has sufficient pneumatic stiffness to resist stretching or expanding throughout the expected pressure range. Also, the problem of seal blow-out is virtually eliminated. Additionally, the rolling seal having a U-shaped configuration permits a substantial length of travel of the piston to insure accurate measurements therefrom and prevents bouncing or other adverse effects from external environment.

BRIEF DESCRIPTION OF THE DRAWINGS

FIG. 4 is a cross-sectional view of the device of the present invention with the piston therein at rest.

FIG. 5 is a fragmentary cross-sectional view with the piston in partial ascendancy.

FIG. 6 is a perspective of another embodiment of the present invention in a mode to measure expired breath.

FIG. 7 is a perspective of another embodiment of the present invention in a mode to measure inspired breath while providing means to add oxygen to the inspired air.

DETAILED DESCRIPTION OF THE INVENTION

Figure 1:
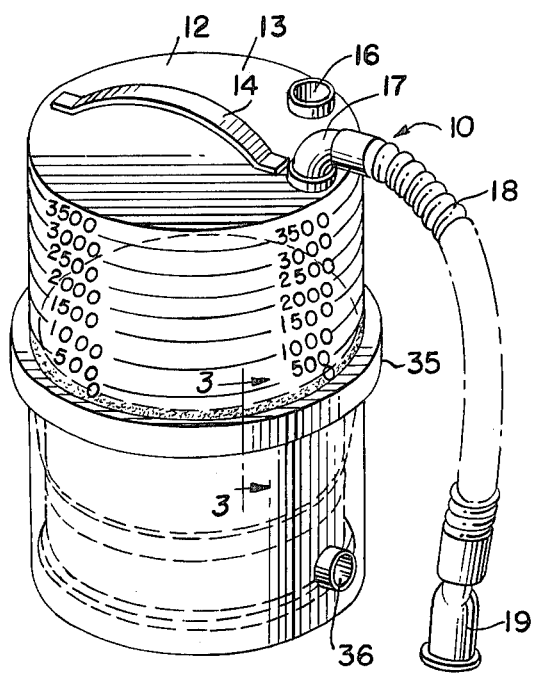
FIG. 1 is a perspective view of the device of the present invention.
Figure 2:
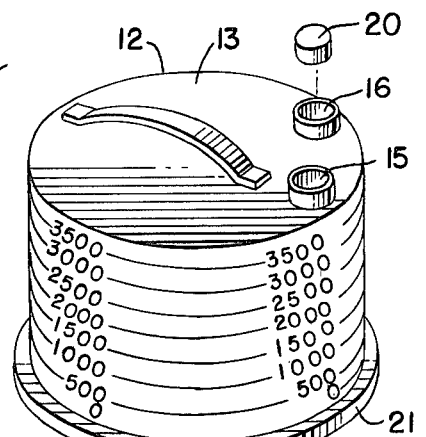
FIG. 2 is an exploded view of the device of the present invention clearly showing some of the component parts.
Figure 2:
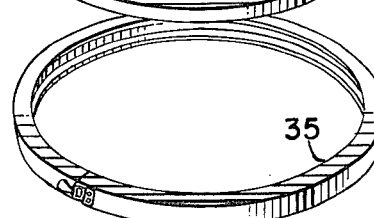
Figure 2:
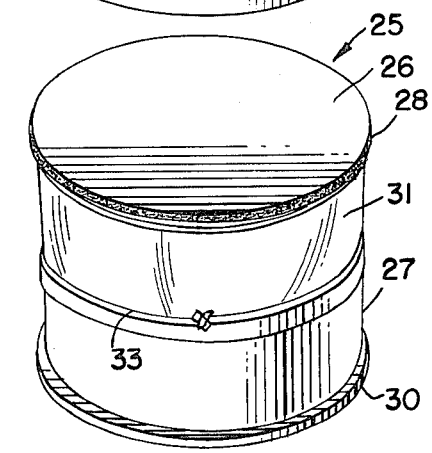

Attention is now directed to FIG. 1 wherein the device of the present invention is identified by reference numeral 10. This figure should be taken in conjunction with FIG. 2 for a good understanding of the invention as this figure illustrates the device in an exploded manner. It will be noted that the device 10 has, generally, a cylindrical configuration. It has an upper cylindrical housing 12, having a top 13. The top 13 has a handle 14, shown as a strap which may be secured to the tops as by rivets, an adhesive or by any suitable convenient means. The strap illustrated is convenient especially with regard to packaging but may take one of a number of suitable forms. Additionally, the top has a first port 15 and a second port 16, both having relatively short upstanding tubular stubs. The ports are designed to accept conduit means. For instance, note from FIG. 1 one end of a tubular elbow 17 has been inserted into the first port 15 in a manner to provide a friction engagement therewith. A corrugated conventional tube 18 is secured to the other end of the elbow 17 by any of a number of conventional well known means. It will be further noted that the tube 18 has at its distal end a mouthpiece 19 affixed thereto as by a friction fit, ultrasonic welding or other conventional well known means. The length of the tube is desirably of sufficient length to enable the patient easy access to the mouthpiece when the device of the present invention is resting on a nearby convenient supporting surface. As in the embodiment of FIGS. 1 and 2 the second port is not used; it may be closed by a plug 20, or may be eliminated.

The cylindrical wall of the upper housing 12 may desirably have graduations to show the amount of air inspired in the manner as will be disclosed hereinafter. As the graduations indicated are over at least the range of 500 to 3500 ml., it should be appreciated that the volume to be encompassed by housing 12 will comprise such a volume.

The upper housing 12 is open at the bottom thereof and terminates in an outwardly radiating annular flange 21.

The device also possesses a lower cylindrical housing 22 having a diameter identical to the upper housing and also possesses substantially the identical volume. The lower housing has a bottom 23 but is open at the top with an outwardly radiating annular flange 24 adapted and constructed at its upwardly facing surface, in one embodiment, to lie in abutment with the downwardly facing surface of the flange 21 on the upper housing when the two housings are assembled.

However, prior to such assembly a hollow piston 25 is positioned internally of said housings. With regard to this portion of the description, attention is also directed to the cross-sectional view of the piston 25 in FIG. 4. The piston 25 has a top 26 of somewhat larger diameter than the outer diameter of the cylinder portion 27 of the piston to thereby provide a flange portion 28. Nevertheless, it has been found appropriate to adjust the diameter of the top 26 of the piston whereby a small but perceptible space is provided between the outwardly facing edge and the inner walls of the aforementioned housings.

The piston 25 at the bottom portion thereof terminates with an annular flange 30 having an outer diameter substantially identical to the flange portion 28 so that it also extends beyond the cylinder portion 27 of the piston but clears the inner walls of the housing to provide a relatively small spacing.

A relatively thin plastic membrane in the form of a sleeve 31 has one end portion secured approximately at the midpoint of the cylinder portion 27 of the piston. The securing thereof may be by different modes. The one shown in the figures has proven to be satisfactory. It will be noted that the cylinder portion 27 has been scored with an annular groove 32 (again note especially FIG. 4, but also FIGS. 3 and 5 which illustrate the mentioned groove). One end portion of the sleeve 31 is held in the groove by suitable means such as a string 33 or the like which is tied tightly to compress the said sleeve portion into the groove and retain the sleeve 31 in place. The other end portion of the sleeve is retained between the abutting surfaces of the flange 21 of the upper housing 12 and the flange 24 of the lower housing 22, as can be clearly seen from FIGS. 4 and 5.

It has been found most efficacious to employ a sleeve having a diameter that is sufficient to fit between the abutting surface of the flange 21 of the upper housing 12 and the flange 24 of the lower housing 22. While at the same time the other end of the sleeve 31 has a somewhat reduced diameter whereby it may be fitted to the cylinder portion 27 of the piston in a snug manner at the position mentioned above. Furthermore, in order to insure against undesired air leaks at either end portion of the sleeve, a conventional adhesive should be employed to further secure the sleeve. The linear and axial dimension should be such that no particular stress is presented to the sleeve either in rest mode or fully elevated position of the piston 25.

Figure 3:
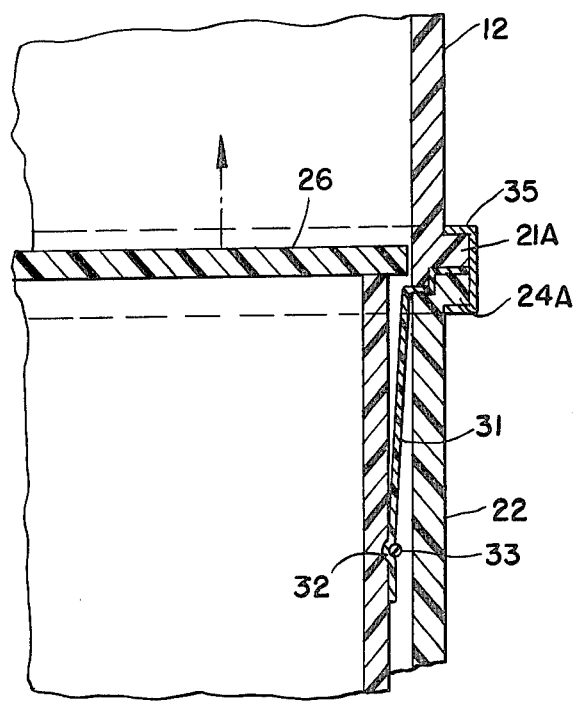
FIG. 3 is a fragmentary cross-sectional view taken along line 3—3 of FIG. 1.
Figure 3:
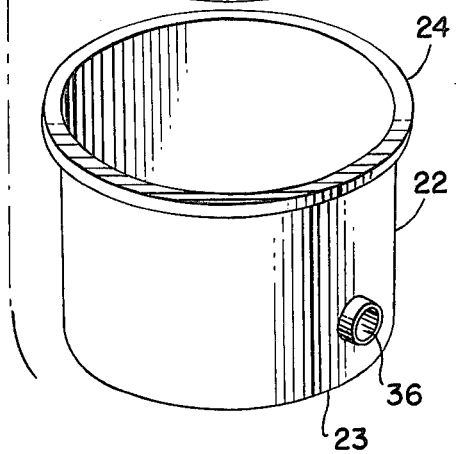

Special note should be made with regard to the embodiment of FIG. 3. It will be noted that the flange 21A of the upper housing and flange 24A of the lower housing are rabbetted to provide complementary mating surfaces thereby providing a greater resistance to lateral motion.

After the assembly of the parts has been completed, a U-shaped strap 35 is secured annularly about the two abutting flanges as illustrated in cross-section by FIGS. 3, 4 and 5. Strap 35 may be constructed of plastic or may be a metal channel. It is contemplated that it be constructed with a connecting linkage means to complete the ring with adjustable features whereby the strap may be tightened or loosened as desired. The latter might occur when it is desired to take apart the device of the present invention for servicing or the like.

The lower housing 22 has a port 36 in the lower cylindrical wall thereof including a small tubular stub. When the embodiment for inspiration of FIGS. 1, 4 or 7 is employed, the port 36 in the lower housing 22 acts to convey ambient air into or out of the housing as necessary. In the modification of use illustrated, generally, by FIG. 6, a corrugated tubular conduit 37 is plugged into the stub of port 36 as the corrugated tubular conduit 37 has at one end a suitable fitment. The distal end terminates in a mouthpiece 38.

Up until this juncture not much has been stated as to the material from which the deivce of the present invention may be constructed, except of course, for the aforementioned retaining strap 35 which has been described as being fabricated of metal. The other components may be preferably constructed of various plastics either of the thermoplastic type or of the thermosetting type. As the strap 14 shown will have a degree of flexibility, although other handles may suffice, a thermoplastic material such as polyethylene or polypropylene will be useful. Also, as the sleeve 31 will be of necessity very flexible, the sleeve should be constructed from a thermoplastic film such as polyethylene. The more rigid elements of the device of the present invention may be constructed of a thermosetting plastic such as any one of a number of well known acrylics. Such plastics besides having good strength characteristics also possess great transparent clarity. This property is especially useful in that when the device is used and the piston rises, it must be seen through the upper housing 12. Of course, other parts of the device may be constructed of translucent plastic or even opaque plastic. For greater visibility the piston should either be colored or at least translucent.

Turning again to the embodiment of FIG. 1, a patient would use the device by inserting the mouthpiece 19 into his mouth. The patient would then inspire thereby creating a partial vacuum in the device as diagrammatically illustrated in FIG. 4. As a result the piston 25 will be drawn upwardly. The sleeve 31 will act as a rolling seal to prevent ingress of air from the outside. FIG. 5 illustrates in a fragmentary manner the rise of the piston with closer view of the manner in which the sleeve functions to accomplish the desired result. As the patient inspires the piston will rise in an almost frictionless manner. To avoid a vacuum on the other side of the piston, i.e., in the lower housing 22, port 36 permits the ingress of replacement air. The patient will inspire in what would be considered one stroke or breath to the limit of his present ability so that actual good effort or even strain is put on the patient's lungs. When the patient has inspired to his maximum capacity a reading of the amount inspired is taken by matching the graduation indicia with the top of the piston. Thereupon the mouthpiece is removed from the mouth of the patient. As a result, gravity will tend to drop the piston to its at rest position, with replacement air returning to the device through the open exposed mouthpiece. The patient may then use the device in a repeated fashion as long as desired or necessary.

In the embodiment of FIG. 6, the patient exhales strongly into the mouthpiece 38 and thereby raises the piston 25 in the same manner as in the inspiration mode. Again, the volume displaced by the piston may be measured and catalogued for review of progress, if any.

It will be further noted that FIGS. 6 and 7 show on the top 13 of the device utilization of both of the ports. The elbow 40 in these figures has a ball valve 41 and seat therefor which underthe aegis of gravity assumes normally a closed position. The ball valve 41 is secured to a small tether 42 at one end thereof and which has its other end secured to small vertically movable shaft means 43 which passes upwardly through a suitable bore in the elbow. By this arrangement the ball valve may be withdrawn from its seat and out of employment.

When the ball valve is functioning the valve is easily dislodged when a patient inspires air through the elbow 40 or expires breath through port 36.

In the embodiment of FIGS. 6 and 7, the second port 16 has its plug 20 removed and replaced with a T-shaped conduit 44 and is frictionally fitted thereinto. The conduit when fitted with an oxygen tube as in FIG. 7, shown by dotted lines, will normally pass the gas so that it escapes through the conduit. The conduit has at its base portion thereof a normally closed valve; urged into a closed position by helical spring 45 in abutment on plunger means 46. By depressing the plunger 46 the mentioned normally closed valve is opened thereby providing access to the inside of the device.

In the mode of FIG. 7 the patient will inspire the gaseous contents of the device as mentioned heretofore. Upon cessation of inspiration the piston will not return to its normal position of rest as valve 41 will prevent the return of air. The patient, if capable, by depressing plunger 46 will open the valve in the T-shaped conduit 44 to thereby admit oxygen. The oxygen may have medication added thereto so that upon a subsequent inspiration the patient will derive the benefit of oxygen and any medication administered.

When the device is used to measure expiratory or tidal volume of exhaled air, both valves 41 and 46 are in their normal position. The patient exhales maximally into the mouthpiece 38. The patient, or an attendant, after observing and recording the volume of expired air indicated, depresses the plunger 46 in order to unseat the valve, thereby permitting ambient air to enter the upper cylinder via port 16 thereby allowing the piston to return to its normal position. It has been discovered that when the device is used for testing expiratory volume the piston 25 is preferably constructed with an open top while the bottom is closed to permit more accurate measurement of expired air.

The incentive spirometer of the present invention rewards the patient for maximal inspiration or expiration by a clear easily discernible visual display. Systematic use of the device should reduce pulmonary complications. A feature resides in the fact that the patient does not swallow air. The device should be inexpensive and is designed for single patient use. It is also lightweight and highly portable so that it can be readily taken home from the hospital.

What is claimed is:

1. An incentive spirometer for measuring the volume of inspired air or the volume of exhaled air capable of relatively easy assembly comprising an upper cylindrical housing having an internal cylindrical surface, said upper cylindrical housing having an enclosing top, said top having at least one port means providing communication internally of said upper housing and externally thereof and adapted and constructed to receive a tubular means when said incentive spirometer is used for measuring the volume of inspired air, a lower cylindrical housing having an internal cylindrical surface of the same diameter as the cylindrical suface of the upper housing, said lower cylindrical housing having an enclosing bottom said upper housing being open at its bottom, said lower housing being open at its top, said upper housing at its bottom having a first outwardly radially extending annular flange, said lower housing at its top having a second outwardly radially extending annular flange, said first flange and said second flange being in confronting relating relationship mating said upper and lower housings together, means associated with said first and said second flange to secure the upper housing and the lower housing together, a cylindrical hollow free floating piston being positioned in said secured complementary mating upper and lower housings, saidn piston having outwardly radially extending means at the top portion thereof and at the bottom portion thereof, said radially extending means having a diameter slightly less than the diameters of the internal cylindrical surfaces of the upper and lower housings whereby the said extending means act as guide means against the internal cylindrical surface of the upper housing and the internal cylindrical surface of the lower housing to permit virtually frictionless vertical movement when said spirometer is utilized, said piston having an external diameter less than the diameters of the internal cylindrical surfaces of the upper and lower housings whereby an annular space is defined between said piston and said internal cylindrical surfaces of said housings, a flexible imperforate sleeve being positioned in said space, one end portion thereof being annularly secured to approximately the midportion of said piston, the other end portion being affixed between said first and said second flanges of said housings, said sleeve having a length between its attachment on said piston and its attachment between said flanges of approximately one half of the length of said free floating piston, said upper housing having at least a portion that is transparent whereby any vertical movement of the piston in the upper housing may be viewed, said lower housing having at least one port means providing communication internally of said lower housing and externally thereof.

2. The spirometer of claim 1 wherein the means associated with said first and said second flange to secure the upper housing and the lower housing together in an annular clamping means U-shaped in cross-section positioned annularly about said first and second flanges to secure the flanges together and thereby complementarily affixing together said upper housing to said lower housing.

3. The spirometer of claim 1 wherein the confronting flanges are rabbetted.

4. The spirometer of claim 3 wherein said port means on said enclosing top includes a normally closed valve.

5. The spirometer of claim 4 wherein the normally closed valve has means for retaining said valve in an open position.

6. The spirometer of claim 5 wherein the enclosing top has a second port means including a tubular conduit providing communication between internally of said housings and externally thereof, said tubular conduit having a normally closed valve to thereby selectively prevent access internally of said housings, said normally closed valve having means to manually open said valve.

7. The spirometer of claim 6 wherein the port means of said lower housing is in the cylindrical wall thereof.

8. The spirometer of claim 7 wherein the port means of said lower housing includes means to which one end of a tubular means may be affixed.

9. The spirometer of claim 8 wherein the enclosing top has a handle affixed thereto.

* * * * *